United States Patent
Carpenter

(10) Patent No.: US 9,639,091 B2
(45) Date of Patent: May 2, 2017

(54) SYSTEM AND METHOD FOR COLLECTING FLUID SAMPLE FROM MACHINE

(71) Applicant: Caterpillar Inc., Peoria, IL (US)

(72) Inventor: Richard Carpenter, Chillicothe, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 14/794,054

(22) Filed: Jul. 8, 2015

(65) Prior Publication Data

US 2017/0010624 A1  Jan. 12, 2017

(51) Int. Cl.
*B60T 17/18* (2006.01)
*G05D 7/06* (2006.01)
*B64C 39/02* (2006.01)

(52) U.S. Cl.
CPC ......... *G05D 7/0617* (2013.01); *B64C 39/024* (2013.01); *B64C 2201/108* (2013.01); *B64C 2201/128* (2013.01)

(58) Field of Classification Search
CPC .... G05D 7/0617; F16N 31/00; G01C 21/005; B64C 30/024; B64C 39/024; E21B 25/005; B05B 9/007; B60T 17/18
USPC ............... 701/2, 3, 25, 36; 141/86; 244/1 R; 175/24; 303/2
See application file for complete search history.

(56) References Cited

U.S. PATENT DOCUMENTS

| | | | | |
|---|---|---|---|---|
| 3,010,767 A * | 11/1961 | Euga | ...................... | B60T 13/403 303/2 |
| 7,213,621 B1 * | 5/2007 | Chang | ...................... | F16N 31/00 141/297 |
| 8,820,672 B2 | 9/2014 | Erben et al. | | |
| 2009/0045290 A1 * | 2/2009 | Small | ...................... | B64C 39/024 244/135 A |
| 2010/0003577 A1 * | 1/2010 | Eguchi | .............. | H01M 8/04201 429/515 |
| 2011/0127421 A1 | 6/2011 | Finlay | | |
| 2013/0292512 A1 * | 11/2013 | Erben | ................... | B64C 39/024 244/1 R |
| 2014/0190746 A1 * | 7/2014 | Carawan | ............... | E21B 25/005 175/24 |

(Continued)

FOREIGN PATENT DOCUMENTS

| | | |
|---|---|---|
| CN | 104122117 | 10/2014 |
| CN | 104155297 | 11/2014 |
| WO | 2014075609 | 5/2014 |

OTHER PUBLICATIONS

Matej Antos, Drones that can do more than just observe: Water sampling UAV, Jan. 27, 2015, Europe.

(Continued)

*Primary Examiner* — Yuri Kan
(74) *Attorney, Agent, or Firm* — William R. Tinker; Jeff A. Greene

(57) ABSTRACT

A system for collecting a fluid sample from a machine having a fluid module is provided. The system includes a docking station disposed on the machine. The system also includes a pump selectively disposed in fluid communication with the fluid module of the machine. The pump is configured to draw a fluid from the fluid module. The system further includes an Unmanned Aerial Vehicle (UAV). The UAV is configured to detachably dock onto the docking station. The UAV is also configured to collect the fluid sample from the pump.

17 Claims, 4 Drawing Sheets

(56) References Cited

U.S. PATENT DOCUMENTS

2015/0344136 A1* 12/2015 Dahlstrom ............ B64C 39/024
                                                    701/3
2016/0018224 A1*  1/2016 Isler .................... G01C 21/005
                                                    701/25
2016/0082460 A1*  3/2016 McMaster ............... B05B 9/007
                                                    701/2

OTHER PUBLICATIONS

Omar EL Akkad |Kelly Cryderman, Canadian technology and the flight of the drones, San Francisco and Calgary—The Globe and Mail, Apr. 6, 2014.
Andrew Rosenblum| MIT, Drones that can do more than just observe: Water sampling UAV, United States of America.

* cited by examiner

SYSTEM AND METHOD FOR COLLECTING FLUID SAMPLE FROM MACHINE

TECHNICAL FIELD

The present disclosure relates to a system and method for collecting a fluid sample, and more particularly to the system and method for collecting the fluid sample from a machine having at least one fluid module.

BACKGROUND

Machines, such as construction machines make use of oil for various purposes. Over a period of time, properties of the oil used in a machine may change or the oil may be contaminated by foreign particles. It is therefore advisable to perform analysis of the oil in the machine in order to monitor if the oil in the machine is fit for use or if the oil requires replacement. The oil in the machine is monitored at regular scheduled intervals, based on system requirements. For this purpose, oil samples are collected from the machines that are further analyzed.

Current oil sampling process requires personnel to travel to an operating location of the machine and halt machine operation for the oil sampling. This process can cause unnecessary downtime associated with the machine and also waste resources at the operating location. Oil sampling can also be tedious if set procedures are not followed, commonly introducing errors in the process, which is not desirable.

U.S. Pat. No. 8,820,672 describes collection and analysis of environmental samples using an Unmanned Aerial Vehicle (UAV). In some examples, the sample is drawn into engagement with a sensor onboard a UAV by the existing fluid flow generated by a rotor fan through a duct of a ducted fan of the UAV. The quality characteristics of the fluid sample may be physically or wirelessly delivered to a remote location. In some examples, samples are drawn into engagement with the sensor by a flexible tube that is attached to an outer surface of the UAV. The flexible tube may allow the UAV to precisely target and collect samples of dust and moisture and other materials from the ground over which the UAV operates.

SUMMARY OF THE DISCLOSURE

In one aspect of the present disclosure, a system for collecting a fluid sample from a machine having a fluid module is provided. The system includes a docking station disposed on the machine. The system also includes a pump selectively disposed in fluid communication with the fluid module of the machine. The pump is configured to draw a fluid from the fluid module. The system further includes an Unmanned Aerial Vehicle (UAV). The UAV is configured to detachably dock onto the docking station. The UAV is also configured to collect the fluid sample from the pump.

In another aspect of the present disclosure, a method of collecting a fluid sample from a machine having a fluid module is provided. The method includes deploying an Unmanned Aerial Vehicle (UAV) to an operating location of the machine. The method also includes docking the UAV onto a docking station disposed on the machine. The method further includes fluidly connecting a pump with the fluid module of the machine. The system includes controlling the pump to draw a fluid from the fluid module of the machine. The method also includes collecting, via the UAV, the fluid sample from the pump.

In yet another aspect of the present disclosure, an Unmanned Aerial Vehicle (UAV) for collecting a fluid sample from a machine having a fluid module is provided. The UAV includes a body configured to detachably dock onto a docking station disposed on the machine. The UAV also includes a rotor coupled to the main body, the rotor is configured to provide lift and propel the UAV. The UAV further includes a pump disposed on the body. The pump is configured to be selectively disposed in fluid communication with the fluid module of the machine and draw a fluid from the fluid module. The UAV includes a fluid container detachably coupled to the body. The fluid container is disposed in fluid communication with the pump to receive the fluid sample therefrom.

Other features and aspects of this disclosure will be apparent from the following description and the accompanying drawings.

DETAILED DESCRIPTION

Figure 1:
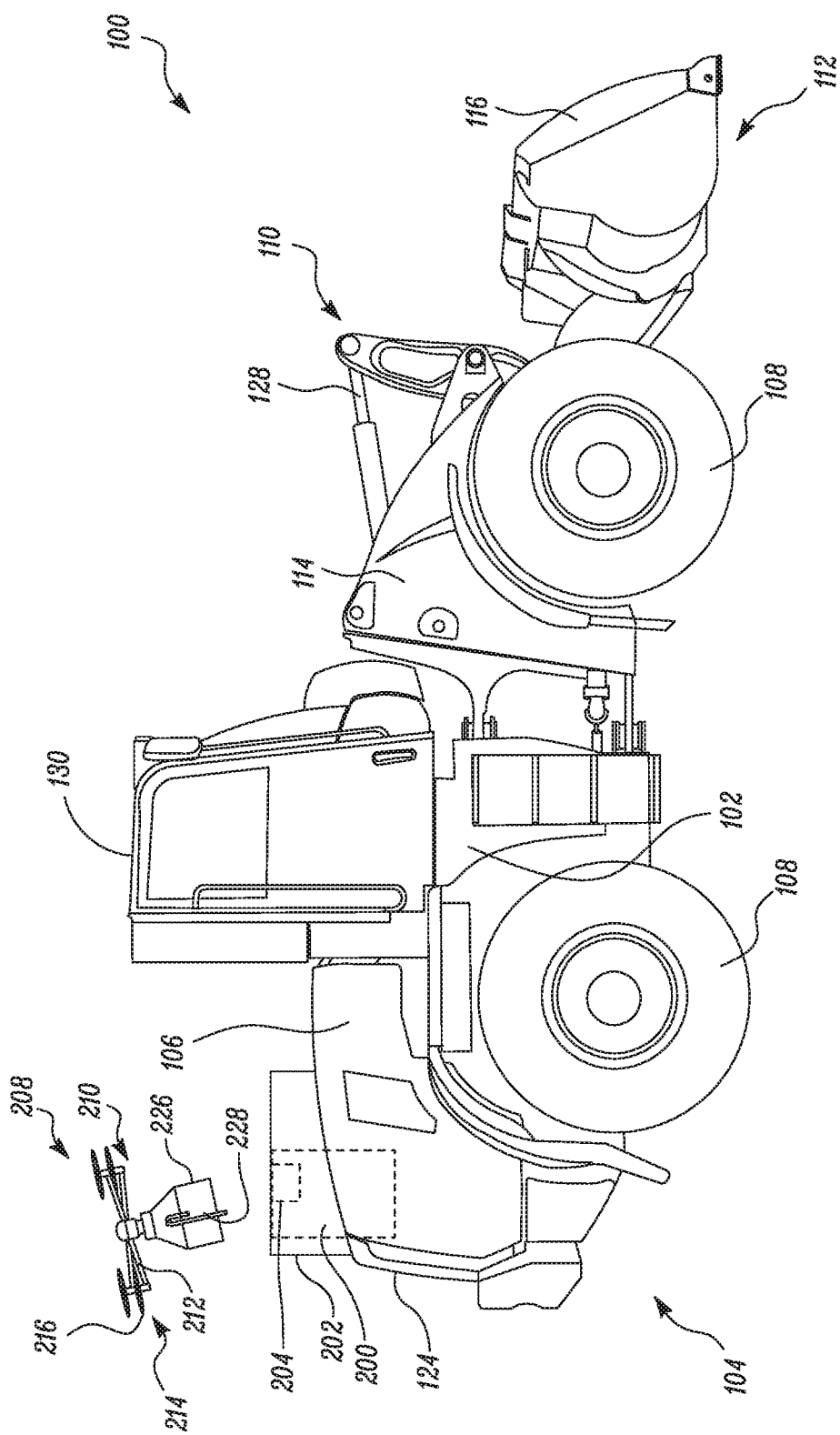
FIG. 1 is a side view of an exemplary machine having a docking station and an Unmanned Aerial Vehicle (UAV), according to one embodiment of the present disclosure.

Wherever possible, the same reference numbers will be used throughout the drawings to refer to the same or the like parts. Referring to FIG. 1, an exemplary machine 100 is illustrated. More specifically, the machine 100 is a compact wheel loader. Alternatively, the machine 100 may be any machine including, but not limited to, a skid steer loader, a backhoe loader, an excavator, a shovel, a dozer, a mining truck, an articulated truck, a track type tractor, a forklift, and a crane. The machine 100 may be any machine known in the art associated with industries including, but not limited to, agriculture, transportation, mining, construction, forestry, and material handling.

The machine 100 includes a frame 102. A power source (not shown) is provided at a rear section 104 of the machine 100. More particularly, the power source is provided within an enclosure 106. The power source may be any power source known in the art, such as, an internal combustion engine, an electric motor, power storage device like batteries, and a hybrid engine. The power source is configured to provide power to the machine 100 for operational and mobility requirements. The machine 100 includes a set of ground engaging members 108, herein embodied as wheels. In another example, the ground engaging member 108 may include tracks. The ground engaging members 108 are configured to provide mobility to the machine 100. The machine 100 also includes a drivetrain (not shown) coupled to the power source and the ground engaging members 108. The drivetrain may include a transmission system having one or more gears, shafts, differentials, torque convertor, hydraulic pump or motor, and so on. The drivetrain may be configured to transmit motive power from the power source to the ground engaging members 108.

The machine 100 may include one or more work implements pivotally coupled to the frame 102. In the illustrated embodiment, a linkage assembly 110 is provided at a front section 112 of the machine 100. The linkage assembly 110 includes a linkage member 114. The linkage member 114 is pivotally coupled to the frame 102. A work implement 116, hereinafter referred to as implement 116, is pivotally coupled to the linkage member 114. The implement 116 may be configured to collect, hold, and convey material and/or heavy objects on the ground. Alternatively, the implement 116 may include any one of a bucket, an auger, a blade, a fork, a hammer, a ripper, or any other known work implement. The linkage assembly 110 is configured to perform tasks such as, earth moving, excavation, digging, demolition, and the like. Further, the linkage assembly 110 may be controlled electrically, mechanically, hydraulically, pneumatically, or by a combination thereof.

Referring to FIG. 1, the linkage assembly 110 includes hydraulic cylinders 128 for providing a required spatial movement to the linkage member 114 and the implement 116. In an alternate embodiment, the linkage assembly 110 may include pneumatic cylinders. In various embodiments, the machine 100 may also include a linkage assembly (not shown) provided at the rear section 104 of the machine 100. The linkage assembly may include an associated work implement (not shown). The machine 100 also includes an operator cabin 130 provided on the frame 102 of the machine 100. The operator cabin 130 includes an operator interface (not shown). The operator interface may include one or more input devices such as pedals, steering, joystick, knobs, levers, switches, display devices, and so on. The input device may assist the operator to operate the machine 100.

The machine 100 may utilize oil for various purposes. Accordingly, the machine 100 may include a number of fluid modules. The fluid modules may store and supply oil to power hydraulic elements of the machine 100. For example, a first fluid module 118 may be associated with the transmission system and provide transmission oil to the same. In a situation wherein the linkage assembly 110 of the machine 100 is hydraulically operated, a second fluid module 120 may be associated with the linkage assembly 110. The second fluid module 120 may be configured to power the hydraulic cylinder 128 of the linkage assembly 110. Further, when the power source associated with the machine 100 is embodied as the engine, a third fluid module 122 may store and supply oil for lubrication purposes of the engine. Based on system requirements, the machine 100 may include more than three fluid modules without any limitations.

The oil in the machine 100 is monitored at regular scheduled intervals to check changes in oil properties and/or an infiltration thereof. For this purpose, oil samples are collected from the machine 100 and are later analyzed. The present disclosure relates to a system 200 for collecting a fluid sample from the machine 100. In one exemplary embodiment, the system 200 is configured to collect oil samples from the machine 100. The system 200 will now be explained with respect to the collection of oil sample from the machine 100. However, the system 200 may be configured to collect coolant samples from the machine 100 or any other fluid sample from the machine 100, based on requirements.

The system 200 includes a docking station 202. The docking station 202 is disposed on the machine 100. In the illustrated example, the docking station 202 is provided at the rear section 104 of the machine 100, and on a hood 124 of the enclosure 106. Alternatively, the docking station 202 may be mounted at a different location, without any limitations.

Figure 2:
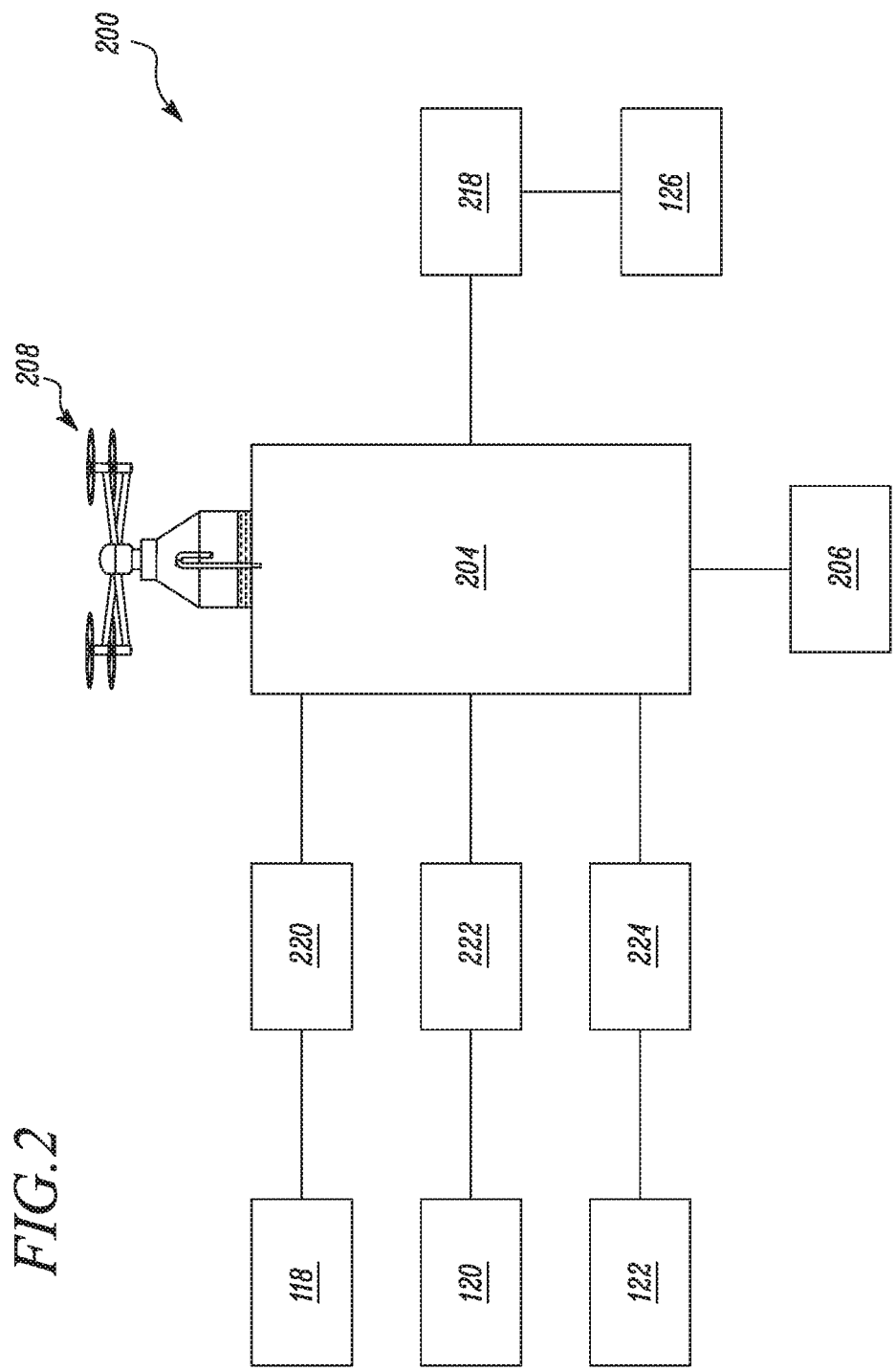
FIG. 2 is a block diagram of an exemplary system for collecting a fluid sample from the machine of FIG. 1, according to one embodiment of the present disclosure.

Referring to FIG. 2, the system 200 includes a pump 204. The pump 204 is provided in selective fluid communication with each of the fluid modules 118, 120, 122 of the machine 100. The pump 204 may be in fluid communication with the respective fluid module 118, 120, 122 via a fluid conduit which will be discussed later. The fluid conduit may be generally present on the machine 100. The pump 204 is configured to pressurize and draw the oil sample from one or more fluid modules 118, 120, 122. The pump 204 may include any known in the art pump. Further, a drive motor 206 is coupled with the pump 204 as shown in FIG. 2 only. The drive motor 206 is configured to drive the pump 204 in order to pressurize and draw the oil sample from one or more fluid modules 118, 120, 122. In one example, the pump 204 may be provided on the machine 100. Alternatively, a pump 204', shown in FIG. 3, may be provided on an Unmanned Aerial Vehicle (UAV) 208.

The system 200 also includes a number of selection valves. The system 200 disclosed herein includes three selection valves, corresponding to the number of fluid modules. More particularly, the system 200 includes a first selection valve 220, a second selection valve 222, and a third selection valve 224. Each selective valve 220, 222, 224 provides selective fluid communication between the pump 204 and the respective fluid modules 118, 120, 122. For example, the first selection valve 220 provides fluid communication between the pump 204 and the first fluid module 118, and so on. The selection valves 220, 222, 224 may embody any known type of valve that selectively allows fluid communication between the pump 204 and the respective fluid modules 118, 120, 122. Each of the selection valves 220, 222, 224 may fluidly couple the pump 204 with one or more locations of the respective fluid modules 118, 120, 122. For example, the first selection valve 220 may fluidly couple the pump 204 with a fluid reservoir (not shown) of the first fluid module 118, a drain portion (not shown) of the first fluid module 118, and the like.

Figure 3:
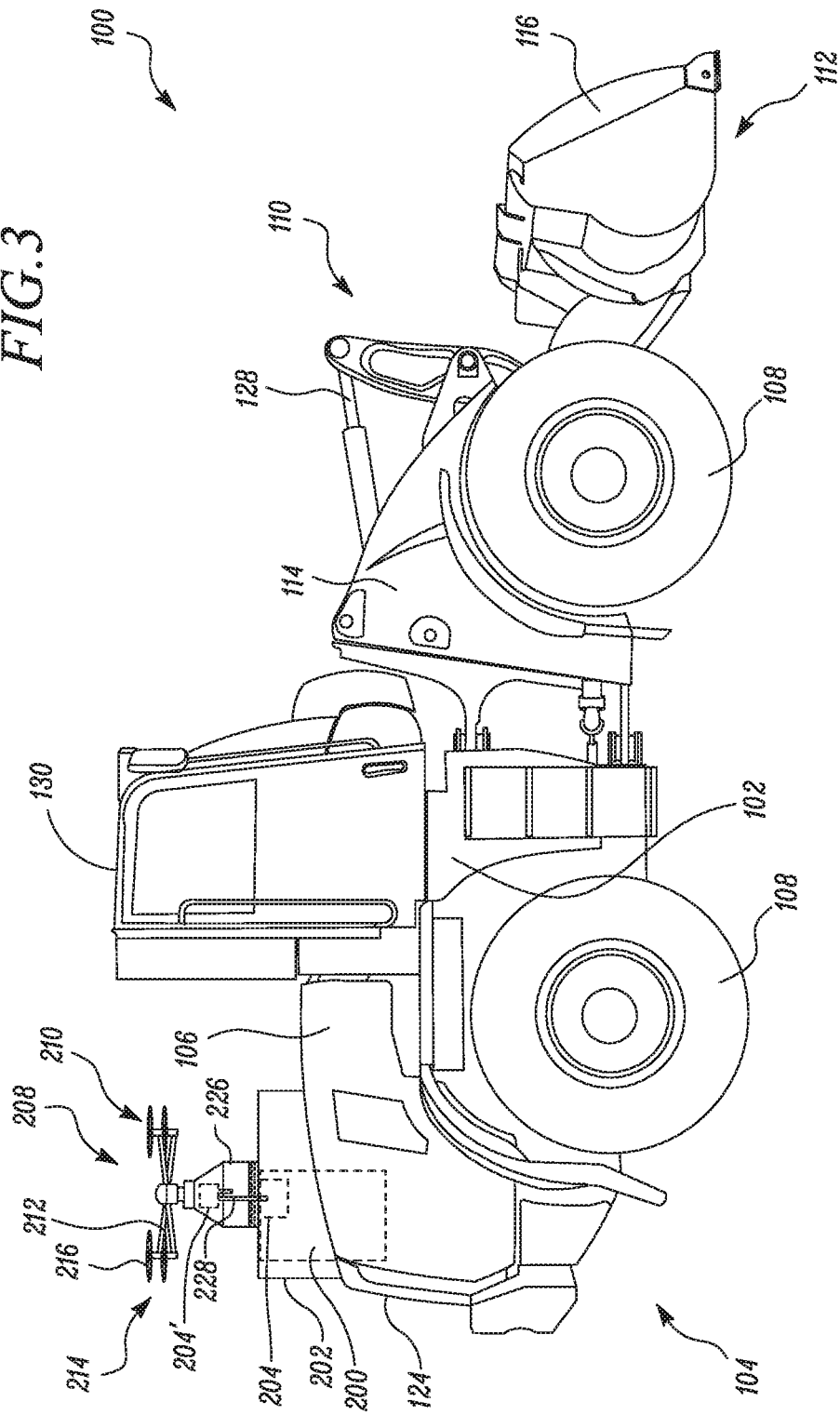
FIG. 3 is a side view of the machine depicting the UAV docked onto the docking station of the machine, according to one embodiment of the present disclosure.

As shown in FIGS. 1 and 3, the system 200 includes the UAV 208. The UAV 208 is configured to be detachably coupled onto the docking station 202 of the machine 100. The UAV 208 is configured to collect the oil sample from the machine 100. More particularly, the UAV 208 is configured to collect the fluid sample received from the pump 204. The UAV 208 docks at the docking station 202 when the oil samples are to be collected from the machine 100. Further, the UAV 208 is configured to detach from the docking station 202 upon collection of the oil sample, and transport the oil sample to a location situated remotely relative to an operating location of the machine 100.

The UAV 208 includes a body 210. The body 210 includes a pair of frame members 212 provided perpendicular to each other. The body 210 is configured to detachably dock onto the docking station 202 provided on the machine 100. The UAV 208 also includes one or more rotors 214 coupled to the body 210 of the machine 100. The UAV 208 shown in the accompanying figures includes four rotors 214. The rotor 214 is coupled to the body 210, and is configured to provide lift and also propel the UAV 208. Each of the rotors 214 include a drive motor (not shown) configured to rotate a propeller 216. In the illustrated embodiment, the UAV 208 includes four propellers 216. Alternatively, the UAV 208 may include any number of propellers 216 based on system requirements. Further, the drive motor may be a variable speed motor such that a speed of rotation of the propeller 216 may be regulated by controlling a speed of the drive motor.

The UAV 208 also includes a control module 218. The control module 218 is communicably coupled with a controller 126 present onboard the machine 100. The control module 218 is configured to receive signals from the controller 126. More particularly, the control module 218 is configured to receive signals indicative of one or more operating parameters associated with the machine 100. In one example, the operating parameter may include speed of the engine that powers the machine 100 or a temperature of the oil in one or more fluid modules 118, 120, 122 of the machine 100. The control module 218 may also receive additional operating parameters other than those listed herein, without limiting the scope of the present disclosure.

Further, the control module 218 may also receive signals from an operator or a control module (not shown) positioned at the remote location. The signals may allow the UAV 208 to be deployed at the operating location of the machine 100 in order to collect the oil samples. The control module 218 may also be configured to store a route map in order to guide the UAV 208 to reach the operating location of the machine 100. In an alternate example, the route map may be retrieved from a database (not shown) that is communicably coupled with the control module 218.

The control module 218 is configured to control the pump 204 to collect the oil sample, based on the operating parameter of the machine 100. More particularly, the oil samples are collected from the pump 204 only when the signals corresponding to the operating parameters received from the controller 126 corresponds to a predetermined value of the operating parameter. Further, in a situation wherein the operating parameter of the machine 100 does not correspond to the predetermined value, the control module 218 is configured to send a signal to the controller 126 of the machine 100 to modify and maintain the operating parameter at the predetermined value. Once the operating parameter is at the predetermined value, the control module 218 actuates and controls the pump 204 to collect the oil sample.

Further, the drive motor 206 associated with the pump 204 is communicably coupled with the control module 218 and is configured to receive signals therefrom. Based on the signals received from the control module 218, the drive motor 206 is configured to drive the pump 204. Additionally, the control module 218 may receive signals pertaining to the current operating parameters of the machine 100 from the controller 126. The signals may assist in analysis of the oil samples taken from the machine 100. The signals are received at the time of collection of the fluid samples from the machine 100. The signals may be indicative of operating hours of the machine 100, temperature of the oil in one or more fluid modules 118, 120, 122 of the machine 100, speed of the engine of the machine 100, and the like.

The system 200 includes a fluid container 226. The fluid container 226 is disposed in fluid communication with the pump 204. The fluid container 226 is configured to receive the oil sample therein. The system 200 may include one or more fluid containers 226 based on the type of application. Further, the fluid container 226 may be appropriately sized to receive and hold sufficient amount of the oil sample therein as per system requirements. As shown in the accompanying figures, the fluid container 226 may be provided on the UAV 208. Alternatively, the fluid container 226 may be provided on the machine 100. The system 200 also includes a fluid conduit 228. The fluid conduit 228 provides fluid communication between the pump 204 and the fluid container 226. At one end, the fluid conduit 228 is coupled with the fluid container 226. Whereas, at a second end, the fluid conduit 228 is configured to be detachably coupled with the fluid container 226. The fluid conduit 228 may embody any one of a hose, tube, pipe, and the like.

In one embodiment, at least one of the pump 204 and the fluid container 226 may be disposed on the machine 100. For example, as illustrated in the accompanying figures, the pump 204 may be provided on the machine 100 whereas the fluid container 226 may be provided on the UAV 208. When the UAV 208 is docked at the docking station 202 (see FIG. 3), the control module 218 (see FIG. 2) may control the operation of the pump 204 (see FIG. 2) in order to pressurize and introduce the oil sample into the fluid container 226. Once the oil sample is received in the fluid container 226, the UAV 208 may detach from the docking station 202 to transport the oil sample to the location situated remotely relative to the operating location of the machine 100.

In another exemplary embodiment, the pump 204 and the fluid container 226 of the system 200 may be provided on the UAV 208 itself. In such an example, when the UAV 208 is docked onto the machine 100, the UAV 208 is configured to fluidly connect the pump 204 with one or more of the fluid modules 118, 120, 122 of the machine 100, through the respective selection valve 220, 222, 224. Based on the fluid communication and the operation of the pump 204, the oil from the respective fluid modules 118, 120, 122 is pressurized and drawn by the pump 204 into the fluid container 226, via the fluid conduit 228.

Alternatively, both the pump 204 and the fluid container 226 may be disposed on the machine 100. Further, based on the signals received by the UAV 208, the UAV 208 may be deployed at the operating location of the machine 100 and docked onto the docking station 202 in order to collect the fluid container 226 from the machine 100. The UAV 208 may dock at the docking station 202 when the machine 100 is operating or stationary, without any limitations. Further, when the operating parameter is at the predetermined value, the pump 204 may be controlled by the control module 218 to draw the oil from the respective fluid modules 118, 120, 122 into the fluid container 226. Upon collection of the fluid container 226, the UAV 208 is configured to detachably couple the fluid container 226 thereto.

In some situations, the hose that connects the pump 204 with the respective fluid module 118, 120, 122 is not purged completely after a previous oil sampling operation such that some quantity of the oil is retained in the hose. In such situations, the oil that first enters the fluid container 226 after the pump 204 is turned on is the oil that is retained within the hose for an unknown amount of time. Such oil may not be an accurate representation of the oil in the fluid modules 118, 120, 122.

The system 200 may therefore benefit from an oil cycling procedure wherein the oil retained in the hose is returned back to the respective fluid modules 118, 120, 122 until fresh oil reaches the pump 204. Accordingly, the system 200 may include suitable means for the oil cycling procedure in order to cycle the oil retained in the hose back to the respective fluid modules 118, 120, 122. Further, in such an example, the control unit 218 of the UAV 208 may be programmed to run the pump 204 for a specified amount of time in order to cycle the oil retained in the hose back to the fluid modules 118, 120, 122, so that a fresh oil sample could be collected into the fluid container 226.

The UAV 208 may then reach the remote location and deposit the oil samples at the remote location for pick up by a person responsible for analysis. In another example, as the oil samples are received at the remote location, the remote location may incorporate oil analysis equipment and automatically process the oil samples. The results obtained after the analysis may be uploaded to a maintenance database and if required an alert may be generated based on the analysis.

In another exemplary embodiment, the UAV 208 may additionally and optionally include an oil analysis module (not shown) present onboard the UAV 208. The oil analysis module may be configured to perform on board analysis of the oil sample that is collected by the UAV 208 for analysis. The oil analysis module may be communicably coupled to the oil within the fluid container 226. In one example, the oil analysis module may include oil quality sensors (not shown). The oil quality sensors may be configured to sense parameters such as nitration, oxidation, viscosity, density, etc. of the oil present in the fluid container 226. In another example, the oil analysis module may include particle counter sensors (not shown). The particle counter sensors may be configured to determine an ISO code of the oil and also type of contaminants in the oil if present.

The oil analysis module may be communicably coupled with the control module 218. In a situation wherein the oil sample is fit for further use, the control unit 218 may send signals to the UAV 208 to return to the machine 100 in order to empty the collected oil sample back to the respective fluid module 118, 120, 122. Alternatively, if the oil sample does not meet system and operational requirements, the UAV 208 may deposit the oil samples at the remote location for further analysis.

The controller 126 and the control module 218 may embody a single microprocessor or multiple microprocessors for receiving signals from components of the system 200. Numerous commercially available microprocessors may be configured to perform the functions of the controller 126 and the control module 218. A person of ordinary skill in the art will appreciate that the controller 126 and the control module 218 may additionally include other components and may also perform other functions not described herein.

INDUSTRIAL APPLICABILITY

The present disclosure relates to the system 200 that is configured to automate the oil sampling process associated with the machine 100. The system 200 includes the UAV 208 that is configured to be deployed automatically or on demand to the machine 100 to collect oil samples. The machine 100 could be running or stationary during the oil sampling process, and the UAV 208 could attach to the docking station 202 to draw out the oil sample at the particular operating condition. Further, the system 200 has capabilities to record machine parameters such as operating hours, engine speed, oil temperature, and the like at the time of the oil sampling process to ensure accuracy in the analysis of the oil sample.

The oil sampling procedure using the system 200 does not require the machine 100 to be halted thereby decreasing the downtime associated with the operation of the machine 100. Further, as the system 200 provides automatic sampling of the oil, the system 200 reduces any human interference and therefore reduces wastage of dealer/site resources. The system 200 also eliminates any errors and is a reliable procedure of collecting the oil samples. The system 200 also includes means to test the oil sample soon after the UAV 208 collects the oil from the machine. The oil sample is tested on board the UAV 208 to decide if the oil sample should be returned back to the respective fluid modules 118, 120, 122 or if the oil should be deposited for further analysis at the remote location.

Figure 4:
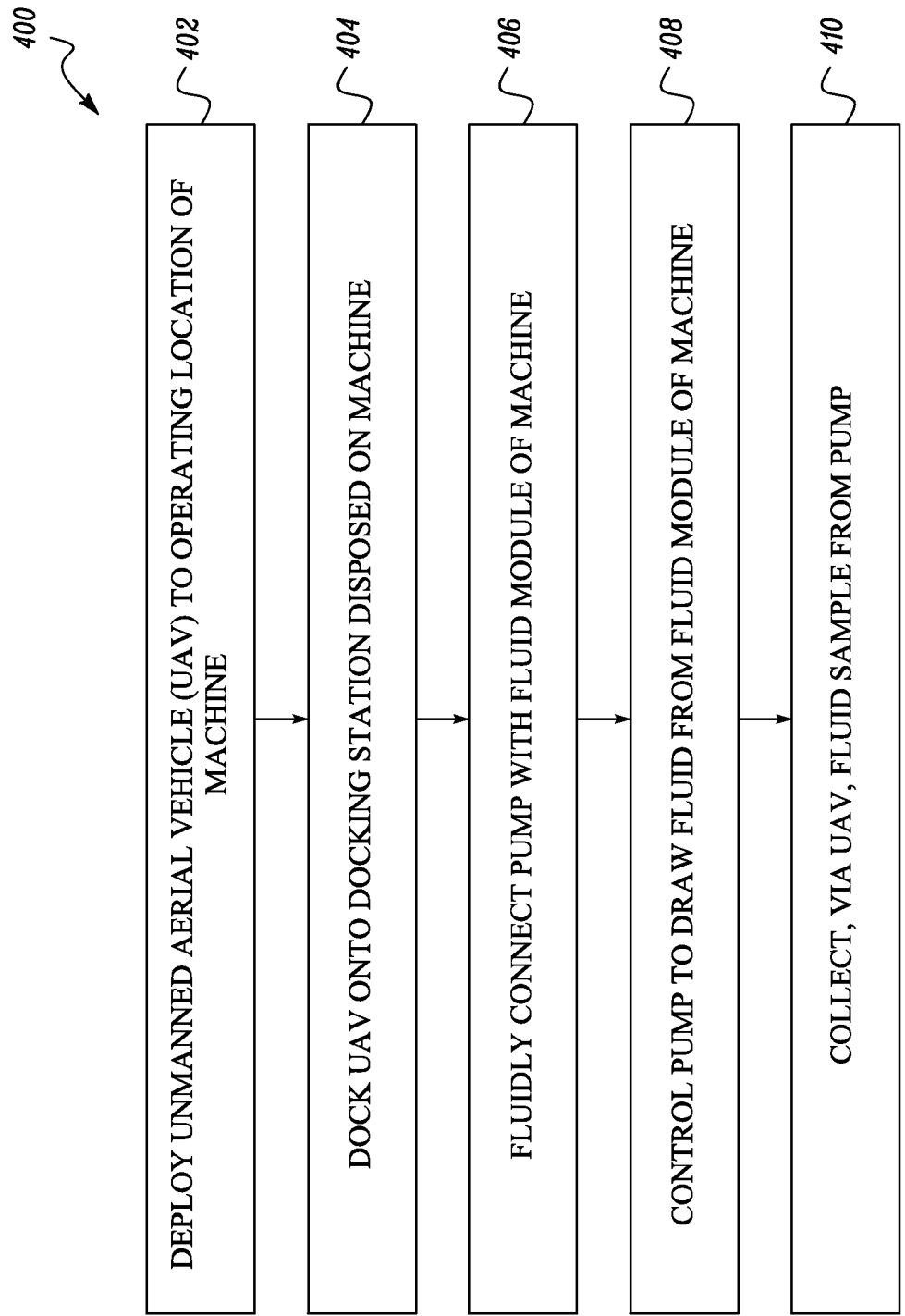
FIG. 4 is a flowchart for a method of collecting the fluid sample from a machine having a fluid module.

FIG. 4 is a flowchart for a method 400 of collecting the oil sample, or any other fluid sample, from the machine 100 having the fluid module 118, 120, 122. At step 402, the UAV 208 is deployed at the operating location of the machine 100. At step 404, the UAV 208 is docked onto the docking station 202 disposed on the machine 100. At step 406, the pump 204 is fluidly connected with the fluid module 118, 120, 122 of the machine 100.

At step 408, the control module 218 is configured to control the pump 204 to draw the fluid from the fluid module 118, 120, 122 of the machine 100. The UAV 208 includes the control module 218. The control module 218 is disposed in communication with the controller 126 associated with the machine 100. The control module 218 receives the signal indicative of the operating parameters of the machine 100 from the controller 126.

The control module 218 controls the pump 204 to collect the oil sample from the machine 100 based on the operating parameter of the machine 100. Further, the controller 126 of the machine 100 is configured to maintain the operating parameter of the machine 100 at the predetermined value. More particularly, the control module 218 controls the pump 204 to collect the oil sample only when the signals pertaining to the operating parameter of the machine 100 received from the controller 126 is at the predetermined value. At step 410, the oil sample is collected via the UAV 208. Further, the collected oil sample is transported via the UAV 208 to the location situated remotely relative to the operating location of the machine 100.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A system for collecting a fluid sample from a machine having a fluid module, the system comprising:
    a docking station disposed on the machine;
    a pump selectively disposed in fluid communication with the fluid module of the machine, the pump configured to draw a fluid from the fluid module; and
    an Unmanned Aerial Vehicle (UAV) configured to detachably dock onto the docking station, the UAV further configured to collect the fluid sample from the pump; and
    a control module disposed in communication with a controller associated with the machine, the control module configured to:
        receive a signal indicative of an operating parameter of the machine; and
        control the pump to collect the fluid sample based on the operating parameter of the machine.

2. The system of claim 1 further comprising a selection valve disposed in fluid communication between the pump and a plurality of fluid modules of the machine, the selection valve configured to fluidly connect one fluid module of the plurality of fluid modules with the pump.

3. The system of claim 1 further comprising a fluid container disposed in fluid communication with the pump, the fluid container configured to receive the fluid sample therein.

4. The system of claim 3, wherein at least one of the pump and the fluid container are disposed on the UAV, and wherein the UAV is configured to fluidly connect the pump with the fluid module of the machine upon docking onto the docking station.

5. The system of claim 3, wherein at least one of the pump and the fluid container are disposed on the machine, and wherein the UAV is configured to detachably couple the fluid container thereto upon collection of the fluid sample.

6. The system of claim 3 further comprising a fluid conduit disposed in fluid communication between the pump and the fluid container.

7. The system of claim 1, wherein the control module is further configured to send a signal to the controller of the machine to maintain the operating parameter at a predetermined value.

8. The system of claim 7, wherein the control module is further configured to control the pump to collect the fluid sample when the operating parameter is at the predetermined value.

9. The system of claim 1 further comprising an electric motor operatively coupled with the pump, the electric motor configured to drive the pump based on a signal received from the control module of the UAV.

10. The system of claim 1, wherein the UAV is further configured to detach from the docking station upon collection of the fluid sample and transport the fluid sample to a location situated remotely relative to the machine.

11. A method of collecting a fluid sample from a machine having a fluid module, the method comprising:
deploying an Unmanned Aerial Vehicle (UAV) to an operating location of the machine;
receiving a signal indicative of an operating parameter of the machine;
docking the UAV onto a docking station disposed on the machine;
fluidly connecting a pump with the fluid module of the machine;
controlling the pump, via a control module, to draw a fluid from the fluid module of the machine based on the operating parameter of the machine; and
collecting, via the UAV, the fluid sample from the pump.

12. The method of claim 11 further comprising maintaining, via the controller of the machine, the operating parameter at a predetermined value.

13. The method of claim 12 further comprising controlling the pump to collect the fluid sample when the operating parameter is at the predetermined value.

14. The method of claim 11 further comprising transporting, via the UAV, the fluid sample to a location situated remotely relative to the operating location of the machine.

15. An Unmanned Aerial Vehicle (UAV) for collecting a fluid sample from a machine having a fluid module, the UAV comprising:
a body configured to detachably dock onto a docking station disposed on the machine;
a rotor coupled to the body, the rotor configured to provide lift and propel the UAV;
a pump disposed on the body, the pump configured to be selectively disposed in fluid communication with the fluid module of the machine and draw a fluid from the fluid module; and
a fluid container detachably coupled to the body, the fluid container disposed in fluid communication with the pump to receive the fluid sample therefrom; and
a control module disposed in communication with a controller associated with the machine, the control module configured to:
receive a signal indicative of an operating parameter of the machine; and
control the pump to collect the fluid sample based on the operating parameter of the machine.

16. The UAV of claim 15, wherein the control module is further configured to send a signal to the controller of the machine to maintain the operating parameter at a predetermined value.

17. The UAV of claim 16, wherein the control module is further configured to control the pump to collect the fluid sample when the operating parameter is at the predetermined value.

* * * * *